US010251598B2

(12) United States Patent
Barnes et al.

(10) Patent No.: US 10,251,598 B2
(45) Date of Patent: Apr. 9, 2019

(54) WAISTBAND MONITORING ANALYSIS FOR A USER

(71) Applicant: CarePredict, Inc., Plantation, FL (US)

(72) Inventors: Ronald A. Barnes, San Antonio, TX (US); David P. Elam, Jr., San Antonio, TX (US); Bennett L. Ibey, San Antonio, TX (US); Ehsaneh Shahhaidar, San Antonio, TX (US); Gerald J. Wilmink, San Antonio, TX (US); Jason B. Wilson, Fair Oaks Ranch, TX (US); Daniel O. Womble, San Antonio, TX (US)

(73) Assignee: CarePredict, Inc., Plantation, FL (US)

( * ) Notice: Subject to any disclaimer, the term of this patent is extended or adjusted under 35 U.S.C. 154(b) by 134 days.

(21) Appl. No.: 15/152,443

(22) Filed: May 11, 2016

(65) Prior Publication Data

US 2017/0325740 A1    Nov. 16, 2017

(51) Int. Cl.
*A61N 1/39* (2006.01)
*A61B 5/11* (2006.01)
*A61B 5/00* (2006.01)
*A61B 5/024* (2006.01)
*A61B 5/0205* (2006.01)
*G06F 19/00* (2018.01)

(52) U.S. Cl.
CPC .......... *A61B 5/486* (2013.01); *A61B 5/0205* (2013.01); *A61B 5/02438* (2013.01); *A61B 5/1112* (2013.01); *A61B 5/1118* (2013.01); *A61B 5/1123* (2013.01); *A61B 5/4809* (2013.01); *A61B 5/4812* (2013.01); *A61B 5/4866* (2013.01); *A61B 5/4875* (2013.01); *A61B 5/6823* (2013.01); *A61B 5/6831* (2013.01); *G06F 19/00* (2013.01); *A61B 5/1117* (2013.01); *A61B 2560/0242* (2013.01); *A61B 2562/0219* (2013.01)

(58) Field of Classification Search
CPC ...... A61B 5/02055; A61B 5/11; A61B 5/1112
USPC .......................................................... 607/6
See application file for complete search history.

(56) References Cited

U.S. PATENT DOCUMENTS

2010/0298899 A1* 11/2010 Donnelly ........... A61B 5/02055
607/6

* cited by examiner

*Primary Examiner* — Carl H Layno
*Assistant Examiner* — Jon Eric C Morales
(74) *Attorney, Agent, or Firm* — DLA Piper LLP (US)

(57) ABSTRACT

Methods, apparatuses, and computer readable mediums for waistband monitoring analysis for a user are provided. In a particular embodiment, a waistband monitoring device is configured to generate a motion pattern based on motion data from a motion sensor coupled to the waistband monitoring device; receive physiological data generated by a physiological sensor coupled to the waistband monitoring device, wherein the physiological data indicates at least one vital sign of the user; identify an activity of the user that corresponds to the motion data and the physiological data; and generate an analysis of the user's performance of the identified activity based on the motion data and the physiological data.

17 Claims, 11 Drawing Sheets

WAISTBAND MONITORING ANALYSIS FOR A USER

BACKGROUND

Technical Field

The field of the invention is data processing, or, more specifically, methods, apparatuses, and computer readable mediums for waistband monitoring analysis for a user.

Background Art

Every year data processing devices are able to be produced in smaller sizes with more processing power. The effect of the manufacturing trend toward small sensors and processors has brought about a change in not only the capabilities of machines in some product categories, but also the factors that are considered in judging the value of such machines. For example, in the personal health monitoring market, with the advent of wearable health monitoring devices, the traditional assessment of a health monitoring device based on the accuracy and precision of its measurements was supplanted by the excitement of such device's smaller sizes and unique monitoring locations. After the excitement of the wearable aspect of a health monitoring device subsided, the examination of such devices began to shift to the capabilities of those devices to perform their stated purpose of monitoring the user.

SUMMARY OF INVENTION

Methods, apparatuses, and computer readable mediums for waistband monitoring analysis for a user are provided. In a particular embodiment, a waistband monitoring device is configured to generate a motion pattern based on motion data from a motion sensor the waistband monitoring device; receive physiological data generated by a physiological sensor the waistband monitoring device, wherein the physiological data indicates at least one vital sign of the user; identify an activity of the user that corresponds to the motion data and the physiological data; and generate an analysis of the user's performance of the identified activity based on the motion data and the physiological data.

The foregoing and other objects, features and advantages of the present disclosure will become apparent after review of the entire application, including the following sections: Brief Description of the Drawings, Detailed Description, and the Claims.

DESCRIPTION OF EMBODIMENTS

Figure 1A:
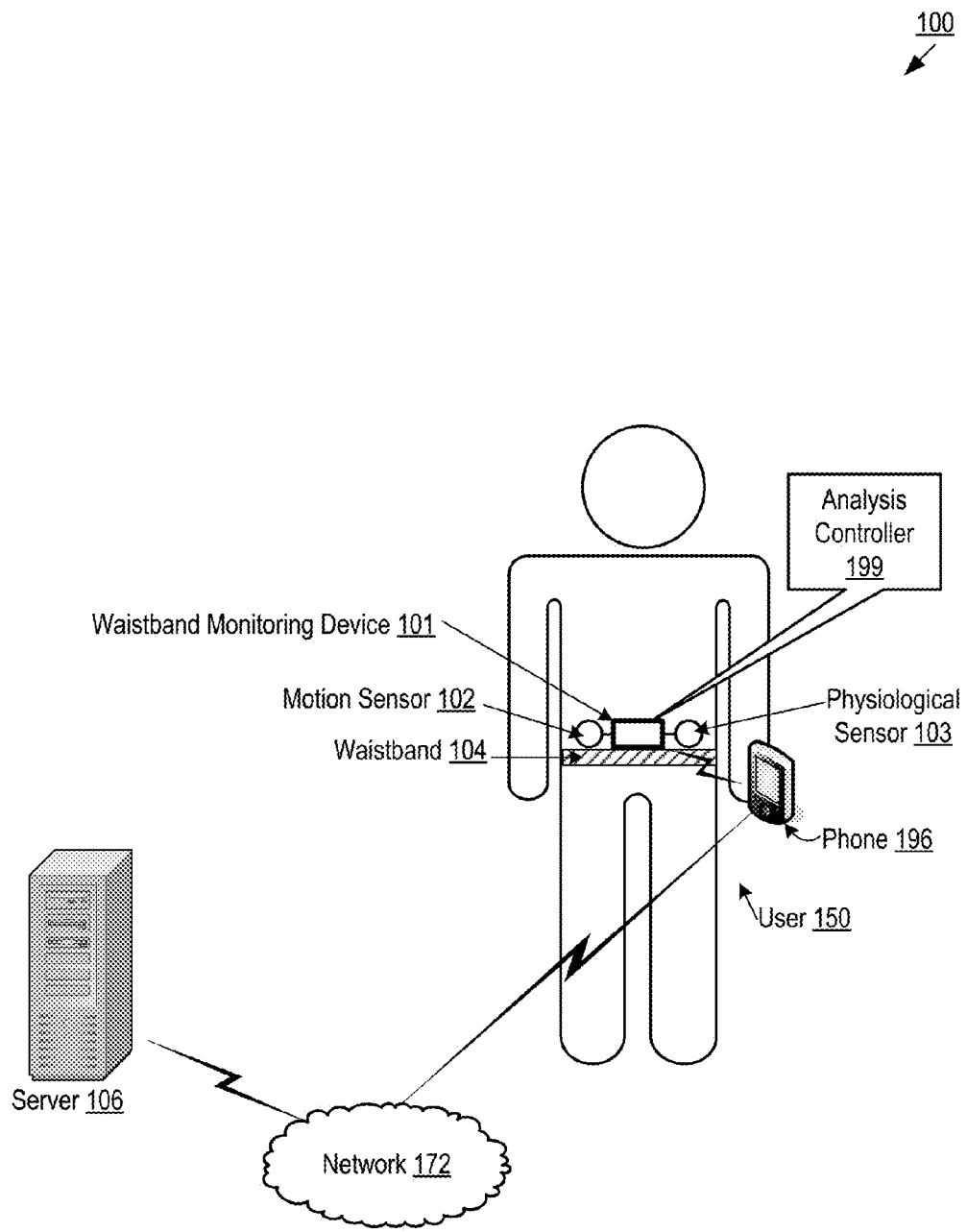
FIG. 1A sets forth a diagram of an illustrative embodiment of an apparatus that includes a waistband monitoring device for waistband monitoring analysis for a user.

FIG. 1A sets forth a diagram of an illustrative embodiment of an apparatus (100) for waistband monitoring analysis for a user (150). In the example of FIG. 1A, the apparatus (100) includes a waistband monitoring device (101), a phone (196), and a server (106).

A waistband monitoring device is a type of wearable device that is coupled to a waistband worn around the waist of a user and is configured to perform waistband monitoring analysis on a user based on data from sensors attached to the waistband monitoring device. As used herein, a waistband refers to a type of garment worn around the waist of a person. Non-limiting examples of waistbands include a fabric strap, the lining of underwear, or a belt.

In particular embodiments, the location of the waistband monitoring device around the user's waist has benefits over other monitoring locations on a user, such as around the user's wrist. The waist is near the center of human body mass and therefore sensors that are part of the waistband monitoring device may more accurately monitor a user's motion and physiological data than from a non-central location, such as the user's wrist. Based on the motion and physiological parameters that are being measured, depending on the application, the location of the waistband monitoring device and sensors may be adjustable with regards to the waistband it is attached to or embedded in. For example, in one configuration the waistband monitoring device may be placed on the left or right side of the user's body and the sensors can be wired out to the center or vice versa.

As part of 'monitoring' a user, a waistband monitoring device may be configured to utilize data from one or more sensors that are either coupled to the waistband monitoring device or are part of the waistband monitoring device. Non-limiting examples of the types of sensors that may be available to a waistband monitoring device include a hydration sensor, a respiration sensor, a heart rate monitor, an ECG monitor, a pulse oximeter, a thermometer, an electromyography (EMG) sensor, an accelerometer, a gyroscope, a Global Positioning System (GPS) location sensor, an environmental condition sensor, humidity sensor, electrodermal activity (EDA) sensor, and many other types of sensors. In the example of FIG. 1A, the waistband monitoring device (101) is coupled to a motion sensor (102) and a physiological sensor (103).

To acquire data from these sensors, a waistband monitoring device may include data acquisition (DAQ) hardware for periodically polling or receiving data from one or more of the sensors available to the waistband monitoring device. For example, circuitry within the waistband monitoring device may monitor the existence and strength of a signal from a sensor and process any signals received from the sensor. The waistband monitoring device (101) may also include circuitry for processing the sensor data. For example, the waistband monitoring device (101) may include circuitry for converting sensor data to another data form, such as motion data, physiological data, or environmental condition data. That is, the waistband monitoring device (101) of FIG. 1A may include the computing components necessary to receive, process, and transform sensor data into a type of data that is usable in a process for waistband monitoring analysis for a user.

In the example of FIG. 1A, the waistband monitoring device (101) includes an analysis controller (199) comprised of automated computing machinery configured for waistband monitoring analysis for the user (150). Specifically, the analysis controller (199) is configured to generate a motion pattern based on motion data from a motion sensor coupled to the waistband monitoring device (101). Motion data is captured or converted data from one or more motion sensors. For example, a motion sensor, such as an accelerometer, may generate motion data, such as acceleration data indicating the motion of the user (150). Continuing with this example, the analysis controller (199) may use the acceleration data or converted data based on the acceleration data to generate a motion pattern.

A motion pattern is a collection of motion data over a period of time. The motion data of a motion pattern may be based on data from multiple sensors and multiple types of sensors. As part of generating a motion pattern, the analysis controller (199) may aggregate sensor data from one or more sensors to generate a collection of motion data over a period of time. For example, a particular generated motion pattern may have first acceleration data generated by an accelerometer on a first axis, second acceleration data generated by an accelerometer on a second axis, third acceleration data generated by an accelerometer on a third axis, and gyroscope data generated by a gyroscope. The motion patterns and/or physiological signals can be personalized for each different user by gathering data from the waistband monitoring device during a short period of time in the beginning as the calibration stage. Machine learning techniques may more accurately identify the specific motion patterns, health conditions, and their changes.

The analysis controller (199) is configured to receive physiological data generated by a physiological sensor coupled to the waistband. Physiological data is data generated from sensors monitoring one or more vital signs of a user. Non-limiting examples of physiological data include hydration measurements, heart rate, oxygen saturation, temperature, muscle contractions, blood pressure, electrodermal activity, and any other types of measurements indicating a vital sign of a person.

In the example of FIG. 1A, the analysis controller (199) is also configured to identify an activity of the user that corresponds to the motion data and the physiological data. An activity may be any type of movement or may be a representation of a state of the user. Non-limiting examples of activities include sleeping and performing exercise activities. Identifying an activity of the user that corresponds to the motion data and the physiological data may be carried out by matching motion data and physiological data to an activity pattern. An activity pattern may specify either a motion pattern or a physiological data pattern or a combination of both. For example, the analysis controller may determine that the user is sleeping based on motion data indicating that the user is lying in a horizontal position and that the user has a particular heartbeat rhythm. As another example, the analysis controller may determine that the motion pattern matches an activity pattern predetermined to correspond with a particular exercise activity. Identifying an activity of the user that corresponds to the motion data and the physiological data may be carried out by receiving an indication from the user that the user is performing a particular activity. For example, the user may select an indication of a particular activity in a graphical user interface of an application executing on a mobile device, such as the phone (196). In this example, the mobile device may provide the indication of the particular activity to the analysis controller (199).

In the example of FIG. 1A, the analysis controller (199) is also configured to generate an analysis of the user's performance of the identified activity based on the motion data and the physiological data. An analysis of the user's performance of the identified activity may be data indicating an evaluation of the motion data and the physiological data. Generating an analysis of the user's performance of the identified activity based on the motion data and the physiological data may be carried out by comparing the motion data and physiological data to one or more performance metrics corresponding to the activity. Examples of performance metrics include measurements for vital signs and data from activity patterns. For example, the analysis controller may determine that a length of time that the user is in a particular sleep stage based on a comparison of the user's measured heart rate to a performance metric indicating a heart rate predetermined to correspond to the user in a REM sleep stage. In this example, the determined length of time that the user is in the particular sleep stage may be indicated within the analysis.

For example, when the identified activity is sleeping, the analysis may indicate at least one of: a total time that the user is asleep; times that the user spent in sleep stages; a time for the user to fall asleep; and an indication of the amount that the user moved while asleep. As another example, when the identified activity is a particular exercise activity, the analysis may indicate one or more of a total time that the user spent performing the exercise activity; and a caloric output that the user expended performing the exercise activity. In a particular embodiment, the analysis may include many comparisons of both motion data and physiological data.

As another example, the analysis controller may determine that the motion pattern matches an activity pattern predetermined to correspond with a particular exercise activity. In this example, the analysis controller may determine differences between the activity pattern and the motion pattern that is based on the user's motion data. The determined differences may be used to analyze the user's performance, such as, but not limited to identifying incorrect performance of an exercise activity, over or under performance of the exercise activity, length of time that the exercise is performed, and number of repetitions of an exercise activity.

As another example, the analysis controller may transmit a visual output to a screen of the waistband monitoring device. In this example, the visual output may display the analysis. Examples of visual output may include a displayed message, an animated avatar, and many others as will occur to Readers of skill in the art.

The analysis controller (199) may also be configured to provide the analysis to another device. For example, the analysis controller (199) may provide the analysis to a server (106) via a network (172). In a particular embodiment, the analysis controller (199) is configured to transmit data to the phone (196) for transmission to the network (172). The server (106) may include an analysis monitor that includes automated computing machinery configured to receive the analysis; the sensor data; and the motion patterns. The analysis monitor may also be configured to act as a database repository for any motion data, motion patterns, physiological data, environmental condition indications, and any other type of data that the analysis controller (199) may utilize to generate an analysis. The analysis monitor may be configured to provide this stored data to the analysis controller. The analysis monitor may also be configured to act as a central repository for multiple users so that users can share performance results, physiological data, sensed data, environmental conditions, and analysis. For example, a user of the waistband monitoring device (101) may forward an analysis to another user or transmit a message encouraging another user along with indications of how the user is performing a particular exercise activity as indicated by the analysis.

Figure 1B:
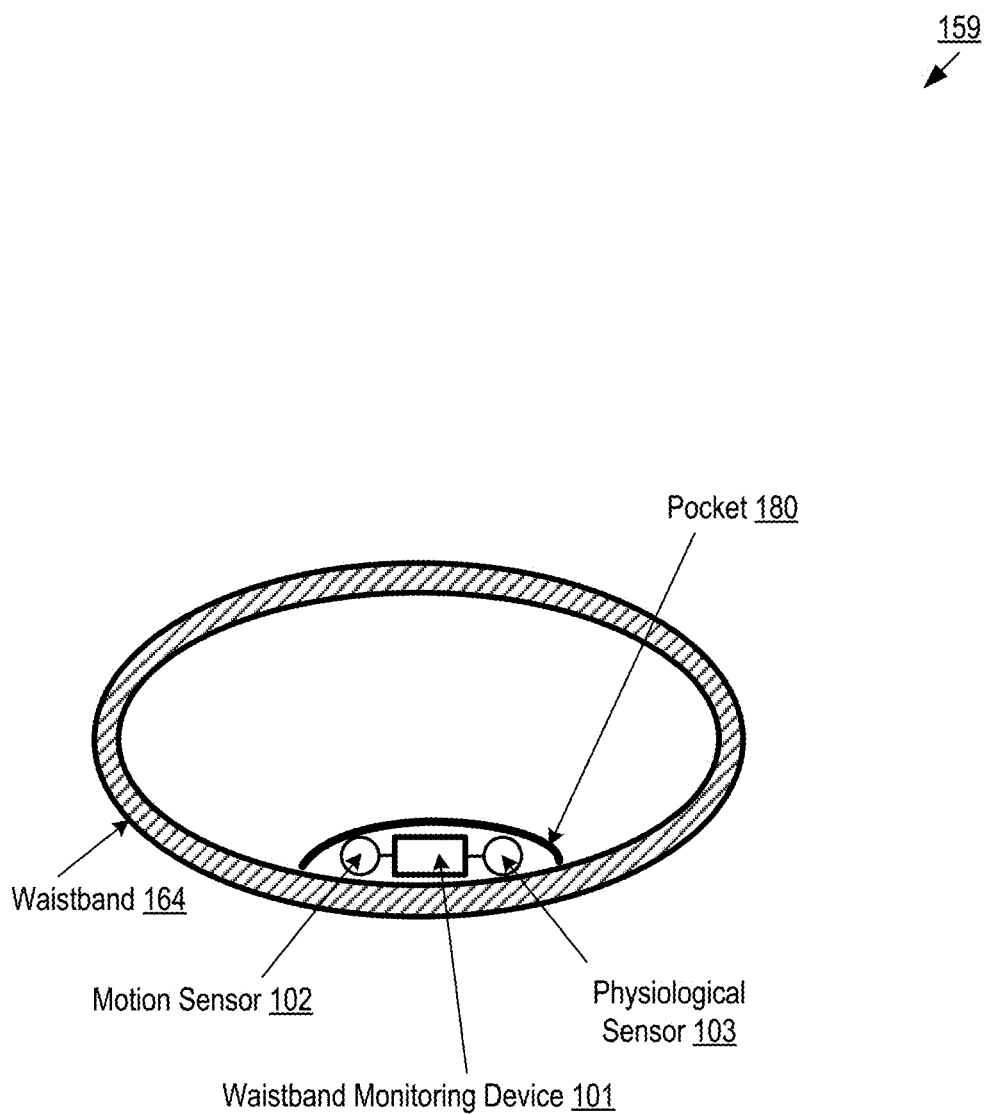
FIG. 1B sets forth a diagram of another illustrative embodiment of an apparatus that includes a waistband monitoring device for waistband monitoring analysis for a user.
Figure 1C:
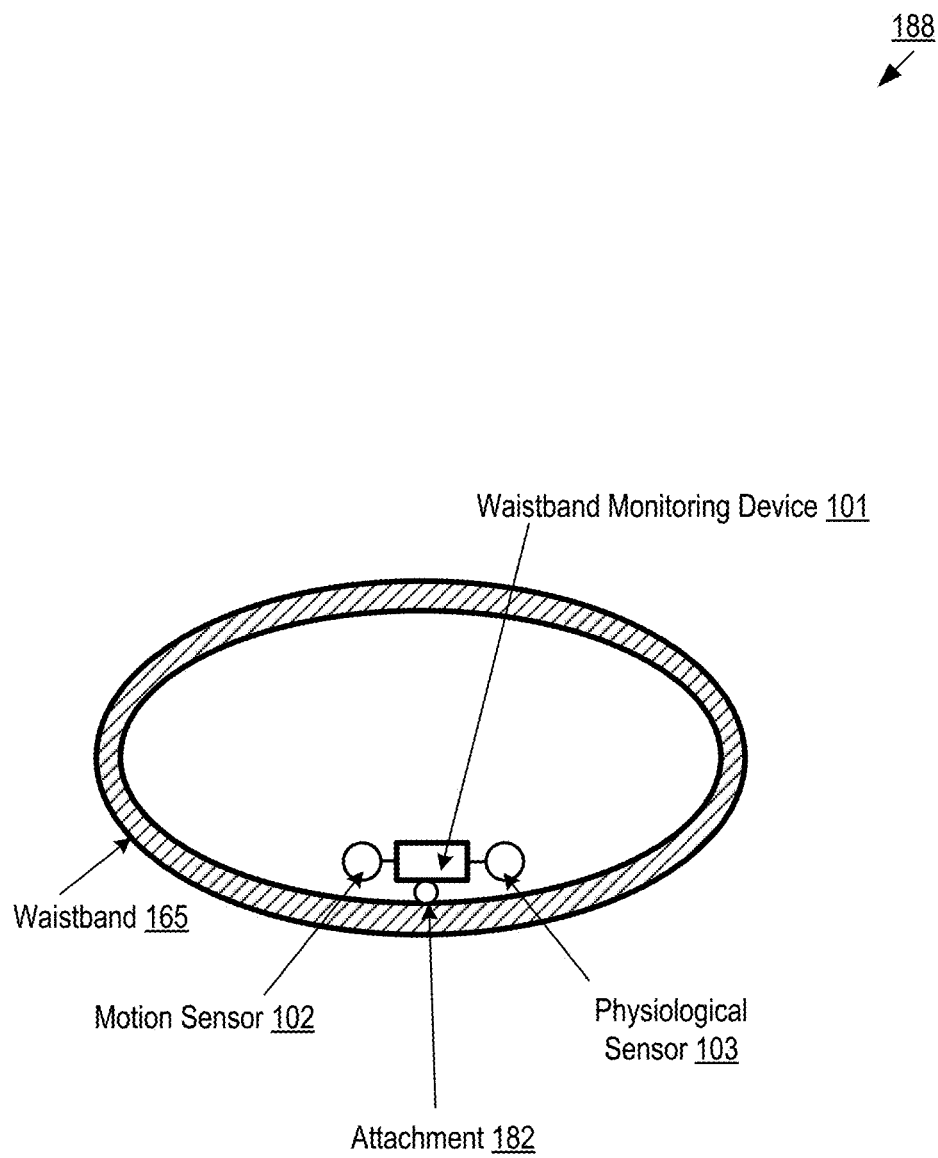
FIG. 1C sets forth a diagram of another illustrative embodiment of an apparatus that includes a waistband monitoring device for waistband monitoring analysis for a user.

A waistband monitoring device may be coupled to a waistband in a variety of ways. FIG. 1B and FIG. 1C each illustrate a particular example of the waistband (104) of FIG. 1A. In the example of FIG. 1B, an apparatus (159) includes a waistband (164) includes a pocket (180). The pocket (180) of FIG. 1B includes an area for placing the waistband monitoring device (101), the motion sensor (102), and the physiological sensor (103). In a particular embodiment, the pocket may be sewn directly into an elastic band of the waistband. The pocket may include a small window to expose the sensors directly to the skin of the user.

In a particular embodiment, the pocket is open on at least one side so that the waistband monitoring device (101), the motion sensor (102), and the physiological sensor (103) may be placed in and out of the pocket. With an open pocket, a user may be able to attach and detach the waistband monitoring device and sensors from the waistband. Alternatively, in another embodiment, the pocket (180) of FIG. 1B is closed on all sides so that the waistband monitoring device (101), the motion sensor (102), and the physiological sensor (103) are integrated into the waistband (164). Readers of skill in the art will realize that multiple variations are possible including but not limited to using multiple pockets to store some or all of the components of the waistband monitoring device (101) and any sensors. Furthermore, the pockets may be located in a variety of locations on or in the waistband. A pocket may be made of a variety of materials including but not limited to the material of the waistband. In addition, the waistband monitoring device and the sensors may also be encapsulated in a soft flexible material which would allow the user to comfortably have the device and sensor around the waist.

In the example of FIG. 1C, an apparatus (188) includes a waistband (165) and the waistband monitoring device (101) that are coupled together with an attachment (182). An attachment is a component used to fasten the waistband monitoring device (101) to the waistband (165). Non-limiting examples of attachments include a clip, a button, or a snap. Readers of skill in the art will realize that the motion sensor (102) and the physiological sensor (104) may also be coupled to the waistband (165) using an attachment. In a particular embodiment, the waistband monitoring device (101) and the sensors (102, 103) are coupled to a waistband using a combination of an attachment and a pocket.

Potential applications of the waistband monitoring device explained here include but are not limited to activity and exercise monitoring, fall detection and prediction, and remote health monitoring. In some health monitoring applications, some parts of the waistband monitoring device, including but not limited to physiological sensors electrodes, may be directly connected to the user's skin. The waistband monitoring device can include other sensors and additional circuitry in order to provide additional information. For example, it can include a proximity touch sensor and an LED or other form of visual indication, such as a screen, to inform the user that the device is in contact with skin, meaning the device is ready to function. In addition, the output of the touch sensor may be used as a trigger to the waistband monitoring device, wherein the waistband monitoring device is in deep sleep, consuming very low power and soon after the touch sensor output showed contact with skin the waistband monitoring device powers up and functions.

Figure 2:
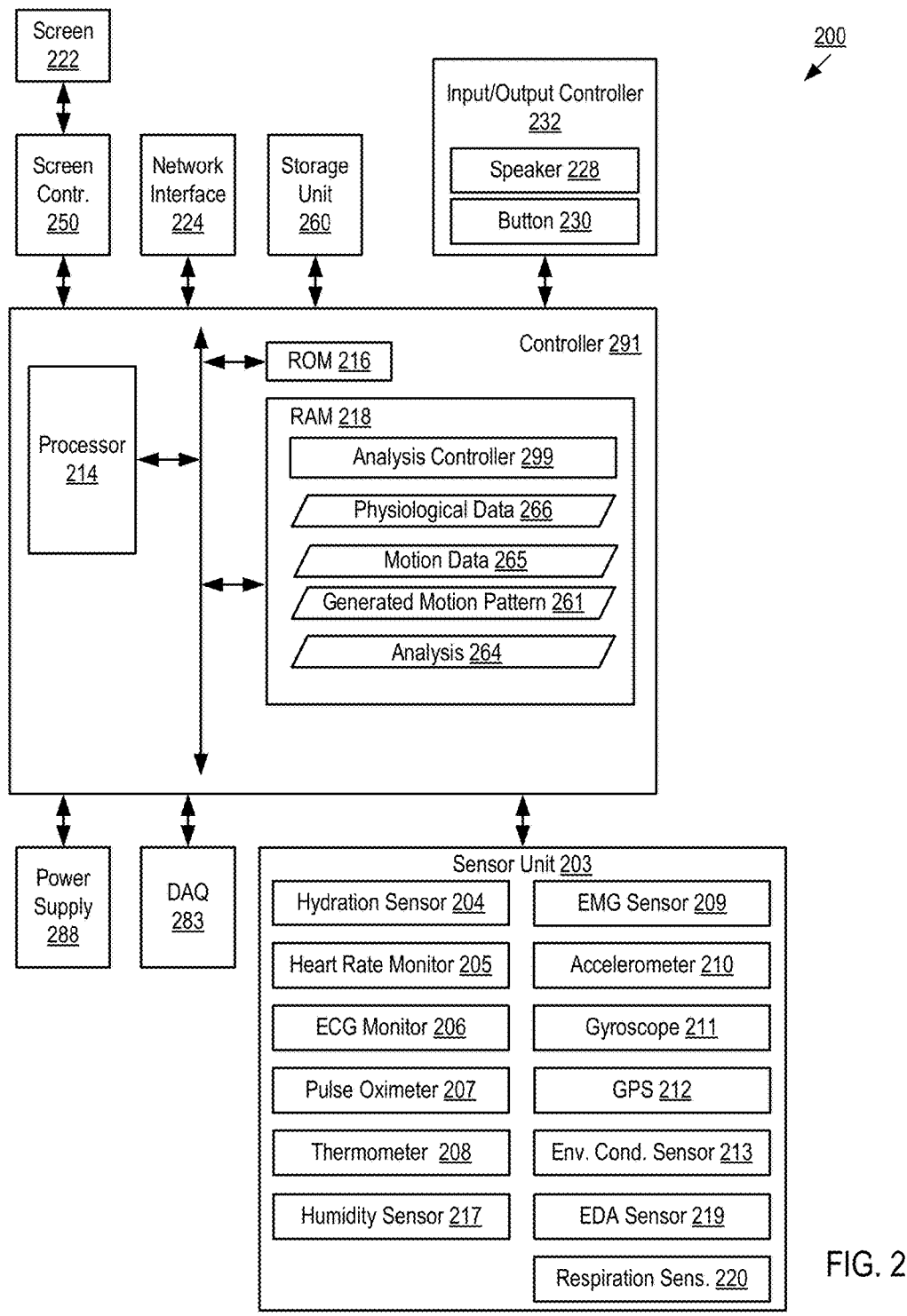
FIG. 2 sets forth a block diagram of another illustrative embodiment of an apparatus that includes a waistband monitoring device for waistband monitoring analysis for a user.

Referring to FIG. 2, an illustrative apparatus (200) for waistband monitoring analysis for a user is shown. The apparatus (200) includes a controller (291) that includes a processor (214), read only memory (ROM) (216), random access memory (RAM) (218). The RAM (218) includes an analysis controller (299). Although, in the example of FIG. 2, the analysis controller (299) is included in RAM (218), Readers of skill in the art will recognize that the analysis controller (299) may be included in other storage locations, such as the ROM (216) and an external storage unit (260), which is coupled for data communications with the controller (291).

In the example of FIG. 2, the apparatus (200) also includes a power supply (288), a screen (222), a screen controller (250), a network interface (224), an input/output controller (232) having a speaker (228) and a button (230), a data acquisition processing unit (DAQ) (283), and a sensor unit (203). The sensor unit (203) of FIG. 2 includes sensors for generating, capturing, and transmitting motion data. In the example of FIG. 2, the sensor unit (203) includes an accelerometer (210), a gyroscope (211), and a global positioning system unit (212).

An accelerometer measures proper acceleration, which is the acceleration it experiences relative to freefall and is the acceleration felt by people and objects. Put another way, at any point in spacetime the equivalence principle guarantees the existence of a local inertial frame, and an accelerometer measures the acceleration relative to that frame. Such accelerations are popularly measured in terms of g-force. Conceptually, an accelerometer behaves as a damped mass on a spring. When the accelerometer experiences an acceleration, the mass is displaced to the point that the spring is able to accelerate the mass at the same rate as the casing. The displacement is then measured to give the acceleration. Modern accelerometers are often small micro electro-mechanical systems (MEMS), and are indeed the simplest MEMS devices possible, consisting of little more than a cantilever beam with a proof mass (also known as seismic mass). Damping results from the residual gas sealed in the device. As long as the Q-factor is not too low, damping does not result in a lower sensitivity. Most micromechanical accelerometers operate in-plane, that is, they are designed to be sensitive only to a direction in the plane of the die. By integrating two devices perpendicularly on a single die a two-axis accelerometer can be made. By adding another out-of-plane device three axes can be measured. Such a combination may have much lower misalignment error than three discrete models combined after packaging. Micromechanical accelerometers are available in a wide variety of measuring ranges, reaching up to thousands of g's.

A gyroscope is a device for measuring or maintaining orientation, based on the principles of angular momentum. Mechanical gyroscopes typically comprise a spinning wheel or disc in which the axle is free to assume any orientation. Although the orientation of the spin axis changes in response to an external torque, the amount of change and the direction of the change is less and in a different direction than it would be if the disk were not spinning. When mounted in a gimbal (which minimizes external torque), the orientation of the spin axis remains nearly fixed, regardless of the mounting platform's motion. Gyroscopes based on other operating principles also exist, such as the electronic, microchip-packaged MEMS gyroscope devices found in consumer electronic devices, solid-state ring lasers, fibre optic gyroscopes, and the extremely sensitive quantum gyroscope. A MEMS gyroscope takes the idea of the Foucault pendulum and uses a vibrating element, known as a MEMS (Micro Electro-Mechanical System). The integration of the gyroscope has allowed for more accurate recognition of movement within a 3D space than the previous lone accelerometer within a number of smartphones. Gyroscopes in consumer electronics are frequently combined with accelerometers (acceleration sensors) for more robust direction- and motion-sensing.

The Global Positioning System (GPS) is a space-based satellite navigation system that provides location and time information in all weather conditions, anywhere on or near the Earth where there is an unobstructed line of sight to four or more GPS satellites. In general, GPS receivers are composed of an antenna, tuned to the frequencies transmitted by the satellites, receiver-processors, and a highly stable clock (often a crystal oscillator).

The sensor unit (203) of FIG. 2 also includes a sensor (213) for generating, capturing, and transmitting environmental condition data. Environmental condition data may include any indications of the environment that the user is performing the activity. In a particular embodiment, environmental condition data may indicate weather conditions, such as humidity level, precipitation measurements, cloud coverage, light, barometric pressure, and temperature. Environmental conditions may also indicate whether the user is inside or outside. For example, a user may provide input to the waistband monitoring device indicating that the user is indoors. In another embodiment, environmental condition data may be measured by the waistband monitoring device. For example, the waistband monitoring device may include a sensor that monitors humidity level or temperature surrounding the waistband monitoring device. In another embodiment, the waistband monitoring device may use one or more network interfaces to receive indications of environmental conditions, such as from a weather indication application, or from a local environmental condition indication device, such as a networked humidity and temperature sensor. A humidity sensor (217) of FIG. 2 is an example of an environmental condiction sensor.

The sensor unit (203) of FIG. 2 also includes sensors for generating, capturing, and transmitting physiological data. In the example of FIG. 2, the sensor unit (203) includes a hydration sensor (204), a heart rate monitor (205), an electrocardiograph (ECG) monitor (206), a pulse oximeter (207), a thermometer (208), an electromyograph (209) for performing electromyography (EMG), an electrodermal activity (EDA) sensor (219), and a respiration sensor (220).

A hydration sensor may be any type of sensor capable of measuring a hydration level of a person. Measuring a hydration level of a person may be performed by a variety of methods via a variety of systems, including but not limited to measuring transepidermal water loss (TWL) with a skin hydration probe. TWL is defined as the measurement of the quantity of water that passes from inside a body through the epidermal layer (skin) to the surrounding atmosphere via diffusion and evaporation processes.

A heart rate monitor (HRM) typically functions by detecting an electrical signal that is transmitted through the heart muscle as the heart contracts. This electrical activity can be detected through the skin. An ECG monitor also generates an activity pattern based on electrical activity of the heart. On the ECG, instantaneous heart rate is typically calculated using the R wave-to-R wave (RR) interval and multiplying/dividing in order to derive heart rate in heartbeats/min. Measuring beat to beat variance of heart rate may also be used to predict the physiological state of a person including: measuring stress, monitoring the state of sleep such as REM and non-REM sleep states.

A pulse oximeter is a medical device that indirectly monitors the oxygen saturation of a user's blood (as opposed to measuring oxygen saturation directly through a blood sample) and changes in blood volume in the skin, producing a photoplethysmogram. A typical pulse oximeter utilizes an electronic processor and a pair of small light-emitting diodes (LEDs) facing a photodiode through a translucent part of the patient's body, usually a fingertip or an earlobe. One LED is red, with wavelength of 660 nm, and the other is infrared with a wavelength of 940 nm. Absorption of light at these wavelengths differs significantly between blood loaded with oxygen and blood lacking oxygen. Oxygenated hemoglobin absorbs more infrared light and allows more red light to pass through. Deoxygenated hemoglobin allows more infrared light to pass through and absorbs more red light. The LEDs flash about thirty times per second which allows the photodiode to respond to the red and infrared light separately. The amount of light that is transmitted (in other words, that is not absorbed) is measured, and separate normalized signals are produced for each wavelength. These signals fluctuate in time because the amount of arterial blood that is present increases (literally pulses) with each heartbeat. By subtracting the minimum transmitted light from the peak transmitted light in each wavelength, the effects of other tissues is corrected for. The ratio of the red light measurement to the infrared light measurement is then calculated by the processor (which represents the ratio of oxygenated hemoglobin to deoxygenated hemoglobin), and this ratio is then converted to SpO2 by the processor via a lookup table.

A thermometer is a device that measures temperature or a temperature gradient using a variety of different principles. A thermistor is an example of a type of thermometer that may be used to measure temperature. A thermistor is a type of resistor whose resistance varies significantly with temperature, more so than in standard resistors. The word is a portmanteau of thermal and resistor. Thermistors are widely used as inrush current limiters, temperature sensors, self-resetting overcurrent protectors, and self-regulating heating elements.

An electromyograph detects the electrical potential generated by muscle cells when these cells are electrically or neurologically activated. The signals can be analyzed to detect medical abnormalities, activation level, or recruitment order or to analyze the biomechanics of human or animal movement.

Electrodermal activity (EDA) is the property of the human body that causes continuous variation in the electrical characteristics of the skin. Historically, EDA has also been known as skin conductance, galvanic skin response (GSR), electrodermal response (EDR), psychogalvanic reflex (PGR), skin conductance response (SCR), and skin conductance level (SCL). The traditional theory of EDA holds that skin resistance varies with the state of sweat glands in the skin. Sweating is controlled by the sympathetic nervous system, and skin conductance is an indication of psychological or physiological arousal. If the sympathetic branch of the autonomic nervous system is highly aroused, then sweat gland activity also increases, which in turn increases skin conductance. In this way, skin conductance can be a measure of emotional and sympathetic responses.

Various methods may be used in order to measure respiration in a respiration sensor. The methods include but are not limited to acoustic sensing of the breathing sound, and sagittal or circumferential movement around the waist during breathing. One example includes measuring the movement of the stomach, sensed by the motion sensors, i.e. accelerometer or gyroscope or combination of both. In another example, the waistband may include conductive wires/materials. Expansion and contraction of the stomach during breathing makes changes in the resistance and inductance of the conductive materials along the waistband (the basis of Respiratory Inductance Plethysmography). MEMS microphones with special filtering circuits may also be used to sense the respiration.

The data acquisition (DAQ) hardware (283) is configured for periodically polling or receiving data from one or more sensors. For example, circuitry within the DAQ (283) may monitor the existence and strength of a signal from a sensor and process any signals received the sensor. The DAQ (283) may also include circuitry for processing the sensor data. For example, the DAQ (283) may include circuitry for conversion of sensor data to another data form, such as motion data, physiological data, or environmental condition data. That is, the DAQ (283) of FIG. 2 may include the computing components necessary to receive, process, and transform sensor data into a type of data that is usable in a process for waistband monitoring analysis for a user.

The analysis controller (299) comprises automated computing machinery configured to perform waistband monitoring analysis. Specifically, the analysis controller (299) is configured to generate a motion pattern (261) based on motion data from a motion sensor; receive physiological data (266) generated by a physiological sensor, wherein the physiological data indicates at least one vital sign of the user; identify an activity of the user that corresponds to the motion data (265) and the physiological data (266); and generate an analysis (264) of the user's performance of the identified activity based on the motion data (265) and the physiological data (266).

The controller (291) is also coupled to a network interface (224), such as an Ethernet port, modem port or other network port adapter. The network interface (224) is adapted to connect to a network and to send data to a recommendation presentation controller or a recommendation evaluation monitor located on a separate device. The network may include one or a combination of any type of network such as LAN, WAN, WLAN, public switched telephone network, GSM, or otherwise.

In a particular embodiment, the power supply (288) may include circuitry used for inductive charging. Inductive charging (also known as "wireless charging") uses an electromagnetic field to transfer energy between two objects. This is usually done with a charging station. Energy is sent through an inductive coupling to an electrical device, which can then use that energy to charge batteries or run the device. Induction chargers typically use an induction coil to create an alternating electromagnetic field from within a charging base station, and a second induction coil in the portable device takes power from the electromagnetic field and converts it back into electrical current to charge the battery. The two induction coils in proximity combine to form an electrical transformer. Greater distances between sender and receiver coils can be achieved when the inductive charging system uses resonant inductive coupling. Recent improvements to this resonant system include using a movable transmission coil (i.e., mounted on an elevating platform or arm), and the use of advanced materials for the receiver coil made of silver plated copper or sometimes aluminum to minimize weight and decrease resistance due to the skin effect.

Figure 3A:
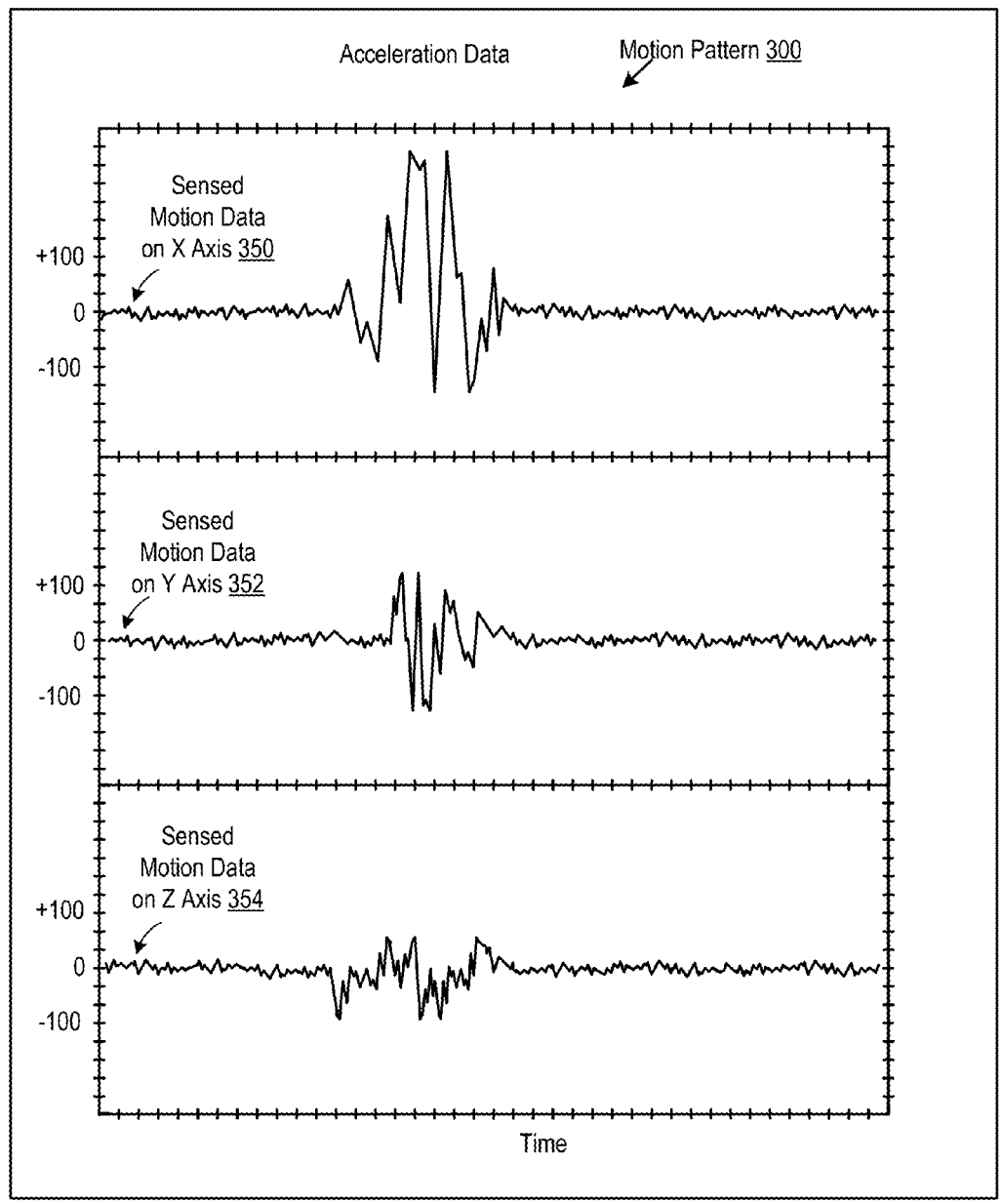
FIG. 3A sets forth a diagram illustrating a time-line of motion data corresponding to an example motion pattern used for waistband monitoring analysis for a user.
Figure 3B:
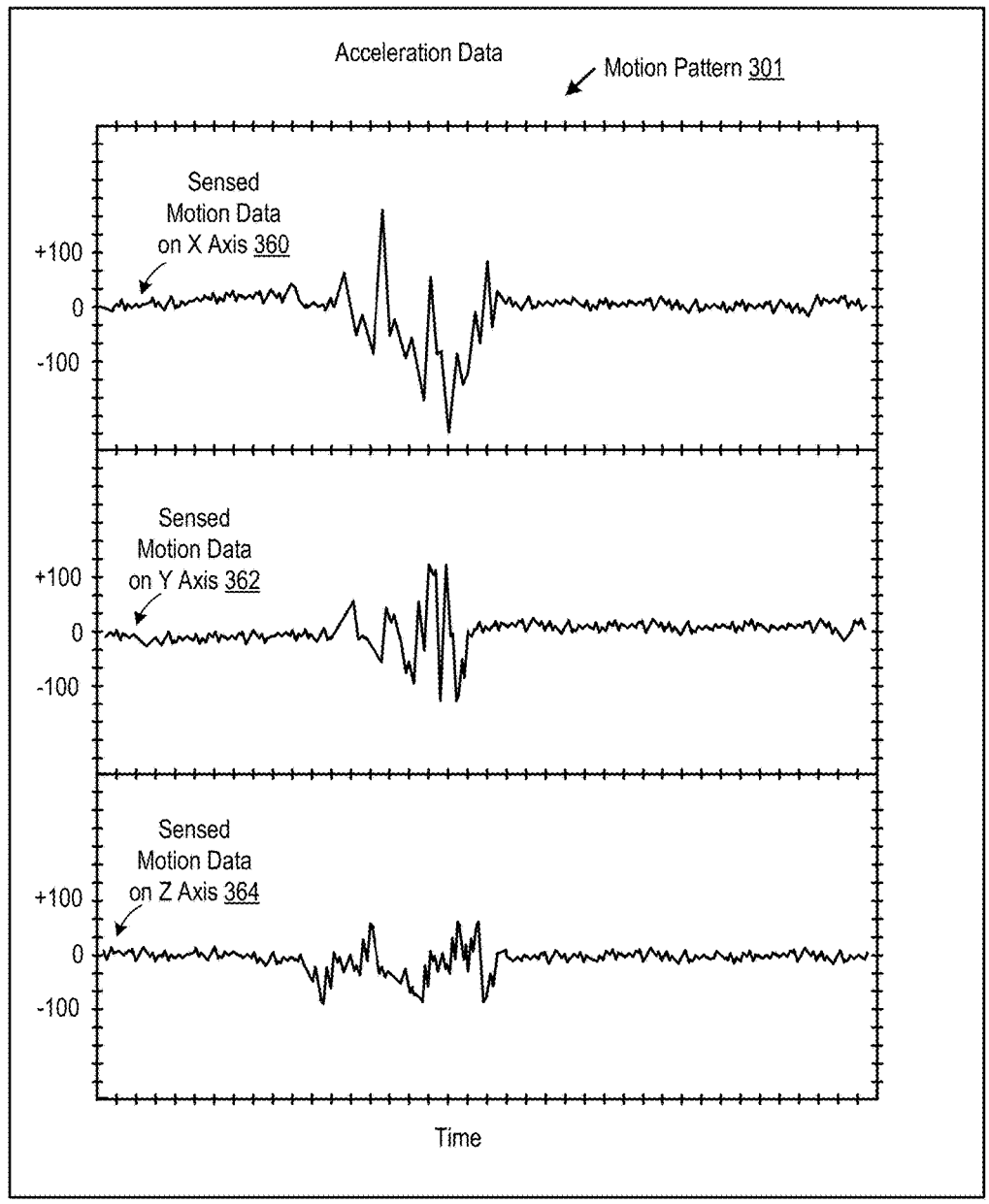
FIG. 3B sets forth a diagram illustrating a time-line of motion data corresponding to another example motion pattern used for waistband monitoring analysis for a user.

For further explanation, FIG. 3A sets forth a diagram illustrating a time-line of motion data corresponding to an example motion pattern (300) and FIG. 3B sets forth a diagram illustrating a time-line of motion data corresponding to another example motion pattern (301). In the examples of FIG. 3A and FIG. 3B, the stored motion patterns (300, 301) includes portions of a collection of acceleration data. Each motion pattern may be an example of a stored motion pattern or a generated motion pattern. According to embodiments, an analysis controller may match a user motion pattern to a stored motion pattern to identify a type of exercise activity that the user is performing.

In the example of FIG. 3A and FIG. 3B, the acceleration data is represented by motion data on the x-axis (350, 360), motion data on the y-axis (352, 362), and motion data on the z-axis (354, 364). Readers of skill in the art will realize, however, that the illustrated motion patterns are only examples and any number of orientations may be used to represent motion patterns. In addition, other types of motion data may be combined to form a motion pattern. For example, gyroscope data may be combined with acceleration data to form a motion pattern.

Figure 4:
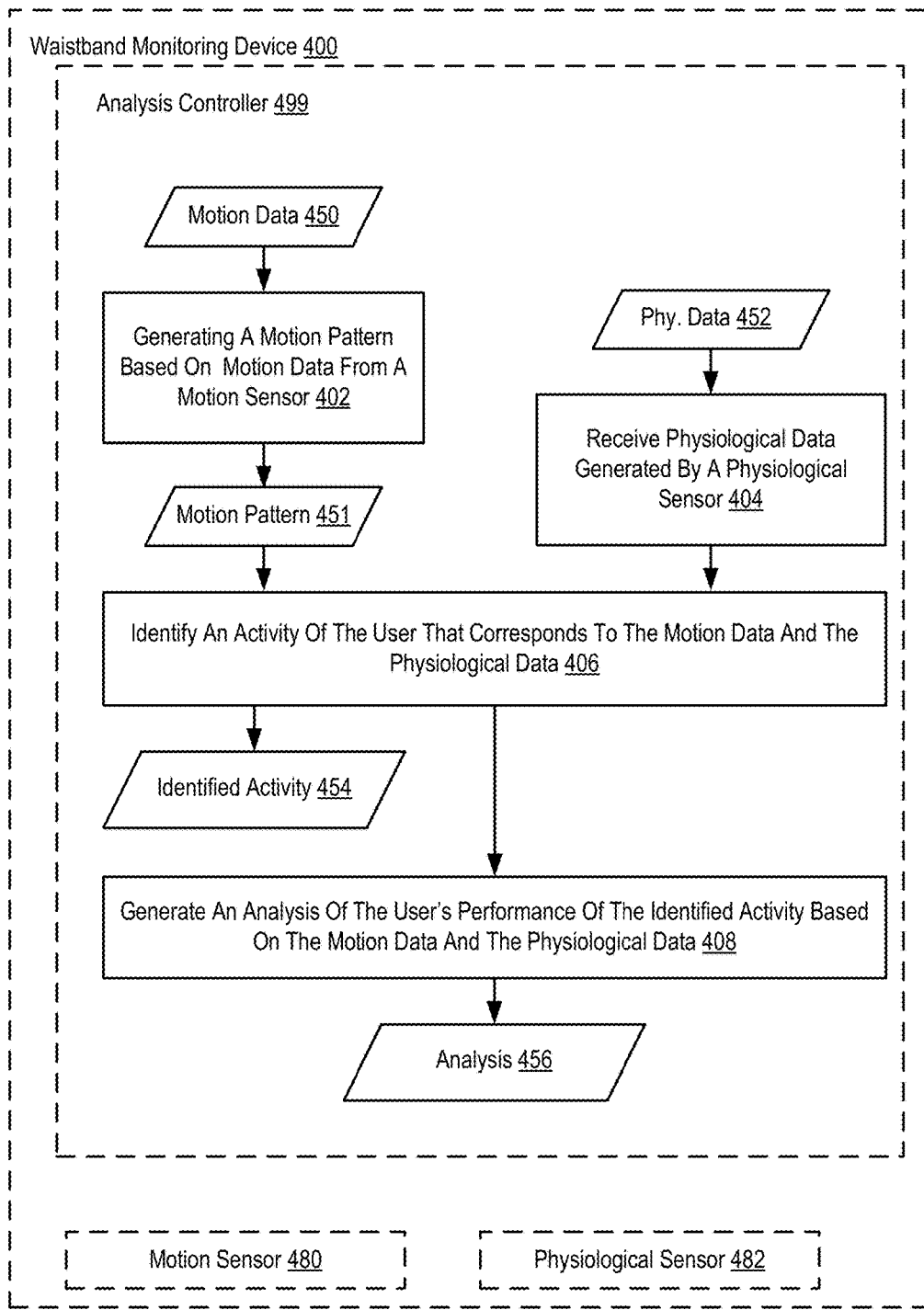
FIG. 4 sets forth a flow chart illustrating an example embodiment of a method for waistband monitoring analysis for a user.

For further explanation, FIG. 4 sets forth a flow chart illustrating an example embodiment of a method for waistband monitoring analysis for a user. The method of FIG. 4 includes an analysis controller (499) generating (402) a motion pattern (451) based on motion data (450) from a motion sensor (480) coupled to the waistband monitoring device (400). Motion data is captured or converted data from one or more motion sensors. For example, an accelerometer may generate acceleration data that indicates the motion of the user (150). Continuing with this example, the analysis controller (499) may use the acceleration data or converted data based on the acceleration data to generate a motion pattern.

According to particular embodiments, a sensor may generate data representing the motion of the user. Non-limiting examples of sensors that can generate sensed motion data include an accelerometer, a gyroscope, an air pressure detector, an inclinometer, and a GPS device. Generating (402) a motion pattern (451) may be carried out by aggregating data from the one or more motion detection devices or sensors and examining the aggregated data to create a pattern of motion. For example, acceleration data from an accelerometer may indicate a horizontal movement and gyroscope data from a gyroscope may indicate a degree of spin along one or more axes. In this example, the analysis controller (499) may combine the acceleration data and the gyroscope data to generate an aggregate pattern of movement.

A motion pattern is a collection of motion data over a period of time. The motion data of a motion pattern may be based on data from multiple sensors and multiple types of sensors. As part of generating a motion pattern, the analysis controller (499) may aggregate sensor data from one or more sensors to generate a collection of motion data over a period of time. For example, a particular generated motion pattern may have first acceleration data generated by an accelerometer on a first axis, second acceleration data generated by an accelerometer on a second axis, third acceleration data generated by an accelerometer on a third axis, and gyroscope data generated by a gyroscope.

The method of FIG. 4 includes an analysis controller (499) receiving (404) physiological data (452) generated by a physiological sensor (482) coupled to the waistband monitoring device (400). Physiological data is data generated from sensors monitoring one or more vital signs of a user. Non-limiting examples of physiological data include hydration measurements, heart rate, oxygen saturation, temperature, muscle contractions, blood pressure, electrodermal activity, respiration measurements, and any other types of measurements indicating a vital sign of a person. Examples of physiological sensors include but are not limited to sensors capable of measuring respiration, hydration, heart rate, oxygen saturation, temperature, muscle contractions, blood pressure, electrodermal activity, and many others that will occur to Readers of skill in the art.

The method of FIG. 4 includes an analysis controller (499) identifying (406) an activity (454) of the user that corresponds to the motion data (450) and the physiological data (452). An activity may be any type of movement or may be a representation of a state of the user. Non-limiting examples of activities include sleeping and performing exercise activities. Identifying an activity of the user that corresponds to the motion data and the physiological data may be carried out by matching motion data and physiological data to an activity pattern. An activity pattern may specify either a motion pattern or a physiological data pattern or a combination of both. For example, the analysis controller may determine that the user is sleeping based on motion data indicating that the user is lying in a horizontal position and that the user has a particular respiration and/or heartbeat rhythm. As another example, the analysis controller may determine that the motion pattern matches an activity pattern predetermined to correspond with a particular exercise activity. As another example, the analysis controller may use heartrate and beat to beat variance of heart rate to predict what state of sleep the user is currently in. Identifying an activity of the user that corresponds to the motion data and the physiological data may be carried out by receiving an indication from the user that the user is performing a particular activity. For example, the user may select an indication of a particular activity in a graphical user interface of an application executing on a mobile device. In this example, the mobile device may provide the indication of the particular activity to the analysis controller (199).

The method of FIG. 4 includes an analysis controller (499) generating (408) an analysis (456) of the user's performance of the identified activity (454) based on the motion data (450) and the physiological data (452). An analysis of the user's performance of the identified activity may be data indicating an evaluation of the motion data and the physiological data. Generating an analysis of the user's performance of the identified activity based on the motion data and the physiological data may be carried out by comparing the motion data and physiological data to one or more performance metrics corresponding to the activity.

Examples of performance metrics include measurements for vital signs and data from activity patterns. For example, the analysis controller may determine that a length of time that the user is in a particular sleep stage based on a comparison of the user's measured heart rate to a performance metric indicating a heart rate predetermined to correspond to the user in a REM sleep stage. In this example, the determined length of time that the user is in the particular sleep stage may be indicated within the analysis.

For example, when the identified activity is sleeping, the analysis may indicate at least one of: a total time that the user is asleep; times that the user spent in sleep stages; a time for the user to fall asleep; and an indication of the amount that the user moved while asleep. As another example, when the identified activity is a particular exercise activity, the analysis may indicate one or more of a total time that the user spent performing the exercise activity; and a caloric output that the user expended performing the exercise activity. In a particular embodiment, the analysis may include many comparisons of both motion data and physiological data.

As another example, the analysis controller may determine that the motion pattern matches an activity pattern predetermined to correspond with a particular exercise activity. In this example, the analysis controller may determine differences between the activity pattern and the motion pattern that is based on the user's motion data. The determined differences may be used to analyze the user's performance, such as, but not limited to identifying incorrect performance of an exercise activity, over or under performance of the exercise activity, length of time that the exercise is performed, and number of repetitions of an exercise activity.

As another example, the analysis controller may determine that a comparison of current motion pattern to the historical motion patterns indicates a change in gait or a reduction in balance. For example, a person suffering from Alzheimer's may experience a subtle but cumulative alteration in gait as the disease progresses. Detecting this change may assist with diagnosis of the disease, or it may assist with assessing whether the person may be at increased risk of falling as evaluated by an objective metric. Alternatively, comparison of the current motion pattern to the historical motion patterns, in an otherwise healthy person, may indicate an acute and sudden loss of balance. In this case, the system may advise the person to sit down or steady themselves before they may become fully aware of the loss of function.

Figure 5:
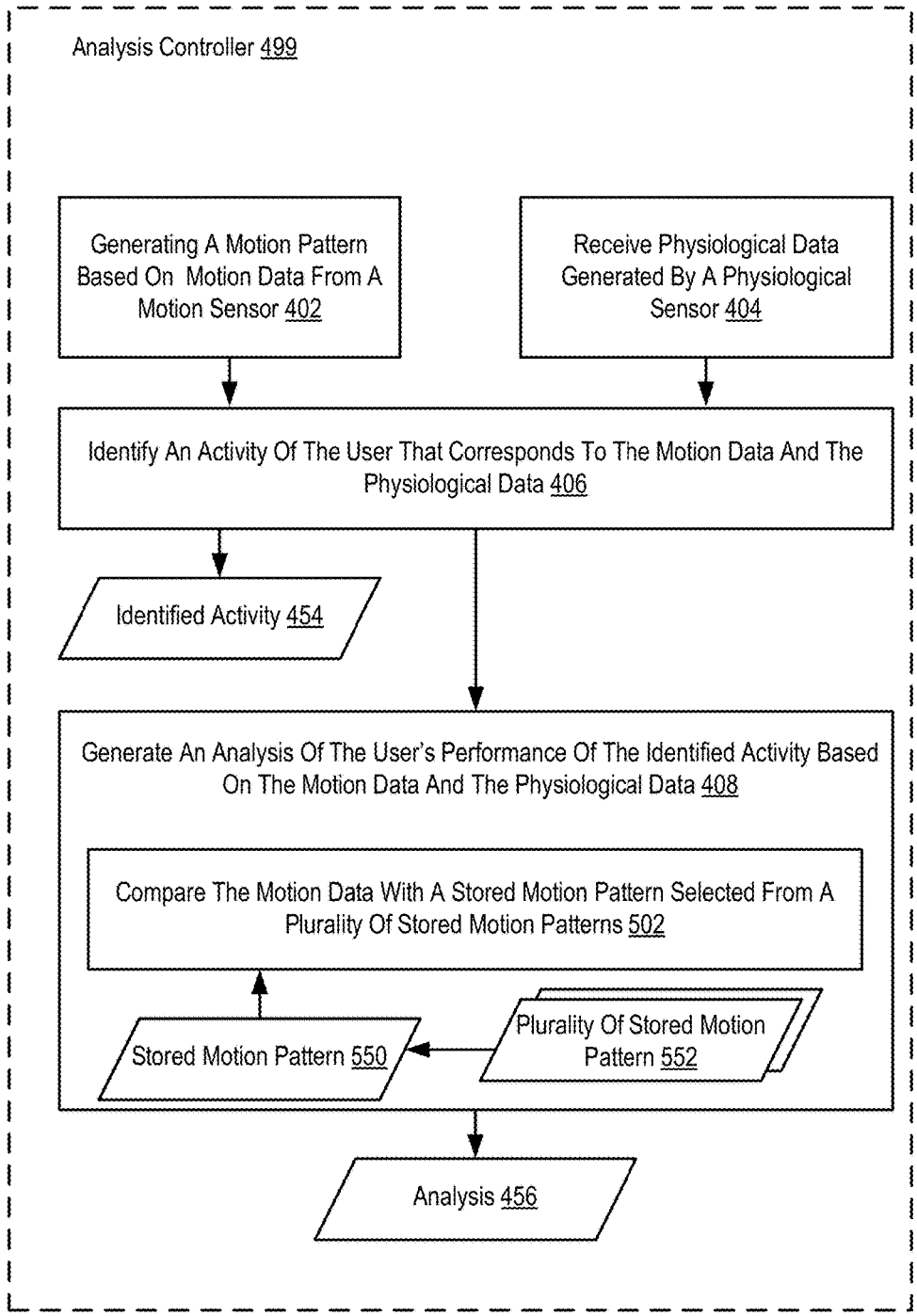
FIG. 5 sets forth a flow chart illustrating another example embodiment of a method for waistband monitoring analysis for a user.

For further explanation, FIG. 5 sets forth a flow chart illustrating another example embodiment of a method for waistband monitoring analysis for a user. The method of FIG. 5 is similar to the method of FIG. 4 in that the method of FIG. 5 also includes generating (402) a motion pattern (451) based on motion data (450) from a motion sensor (480) coupled to a waistband monitoring device (400); receiving (404) physiological data (452) generated by a physiological sensor (482) coupled to the waistband monitoring device (400); identifying (406) an activity (454) of the user that corresponds to the motion data (450) and the physiological data (452); and generating (408) an analysis (456) of the user's performance of the identified activity (454) based on the motion data (450) and the physiological data (452).

In the example of FIG. 5, however, generating (408) an analysis (456) of the user's performance of the identified activity (454) based on the motion data (450) and the physiological data (452) includes comparing (502) the motion data with a stored motion pattern (550) selected from a plurality (552) of stored motion patterns. Each stored motion pattern is predefined to correspond with a particular activity. Specifically, a stored motion pattern includes motion data predetermined to correspond with a particular type of user movement associated with a user performing a specific activity. For example, a first stored motion pattern may include a collection of acceleration data that have previously been determined to correspond with a user walking. In another example, a second stored motion pattern may include a collection of acceleration data that have previously been determined to correspond with a user performing push-ups. By matching the generated motion pattern with a stored motion pattern, the analysis controller (499) may identify the type of activity that the user is performing.

Figure 6:
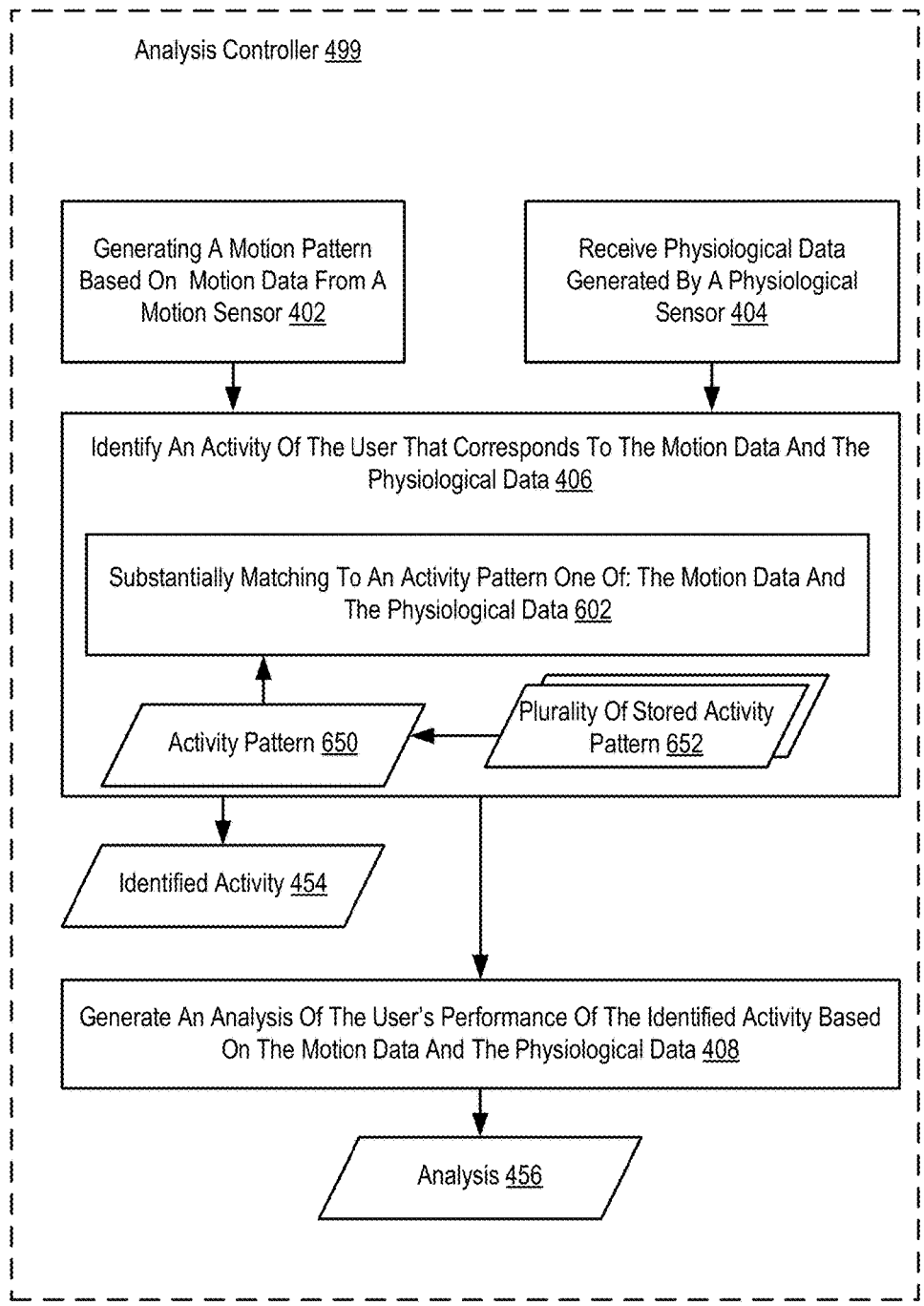
FIG. 6 sets forth a flow chart illustrating another example embodiment of a method for waistband monitoring analysis for a user.

For further explanation, FIG. 6 sets forth a flow chart illustrating another example embodiment of a method for waistband monitoring analysis for a user. The method of FIG. 5 is similar to the method of FIG. 4 in that the method of FIG. 5 also includes generating (402) a motion pattern (451) based on motion data (450) from a motion sensor (480) coupled to a waistband monitoring device (400); receiving (404) physiological data (452) generated by a physiological sensor (482) coupled to the waistband monitoring device (400); identifying (406) an activity (454) of the user that corresponds to the motion data (450) and the physiological data (452); and generating (408) an analysis (456) of the user's performance of the identified activity (454) based on the motion data (450) and the physiological data (452).

In the example of FIG. 6, however, identifying (406) an activity (454) of the user that corresponds to the motion data (450) and the physiological data (452) includes substantially matching (602) to an activity pattern (650) one of: the motion data and the physiological data. An activity pattern may specify either a motion pattern or a physiological data pattern or a combination of both. Substantially matching (602) to an activity pattern (650) one of: the motion data and the physiological data may be carried out by comparing the motion data to the data within the activity pattern and comparing the physiological data to the data within the activity pattern. For example, the analysis controller may determine that the user is sleeping based on motion data indicating that the user is lying in a horizontal position and that the user has a particular heartbeat rhythm.

Figure 7:
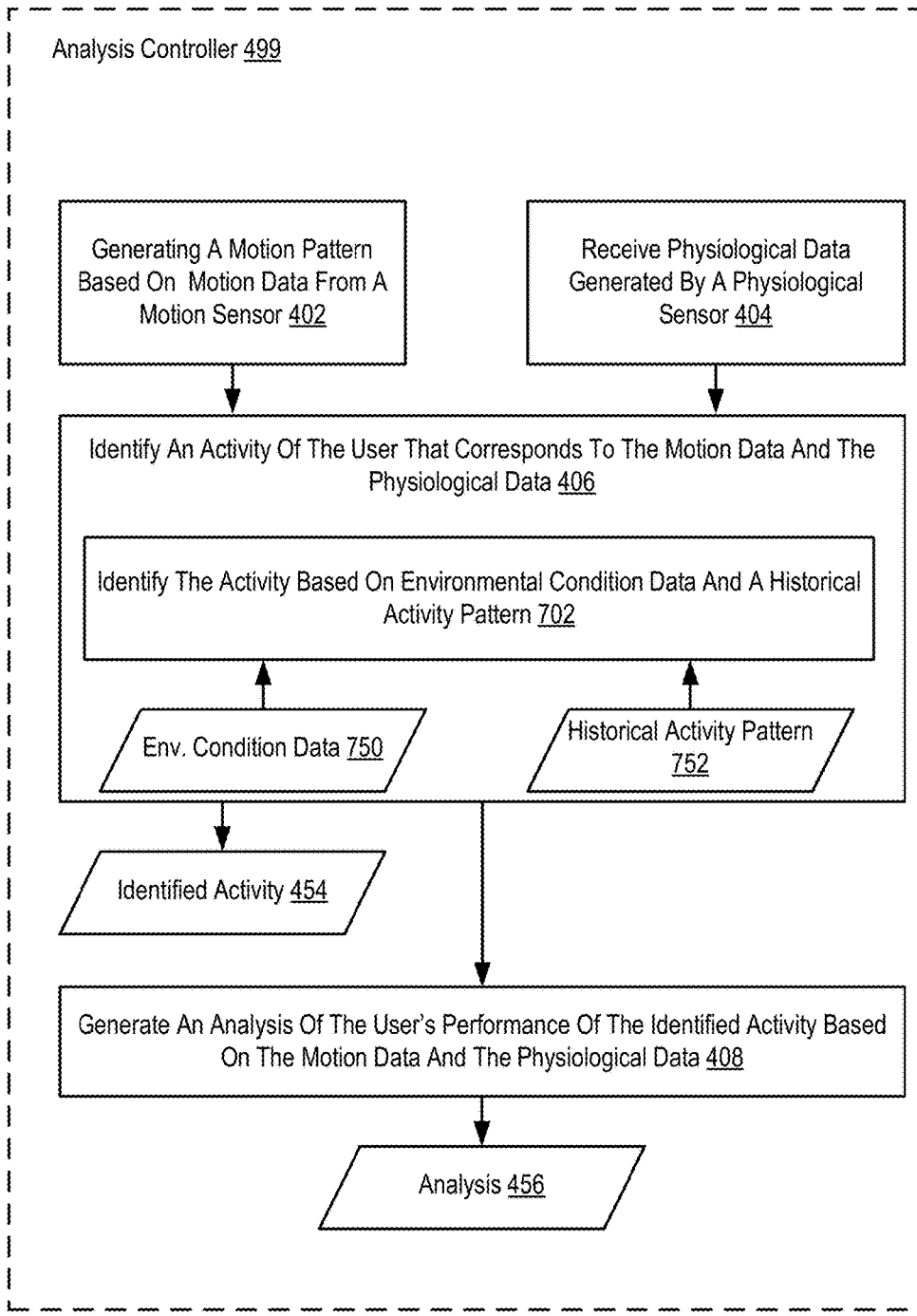
FIG. 7 sets forth a flow chart illustrating another example embodiment of a method for waistband monitoring analysis for a user.

For further explanation, FIG. 7 sets forth a flow chart illustrating another example embodiment of a method for waistband monitoring analysis for a user. The method of FIG. 5 is similar to the method of FIG. 4 in that the method of FIG. 7 also includes generating (402) a motion pattern (451) based on motion data (450) from a motion sensor (480) coupled to a waistband monitoring device (400); receiving (404) physiological data (452) generated by a physiological sensor (482) coupled to the waistband monitoring device (400); identifying (406) an activity (454) of the user that corresponds to the motion data (450) and the physiological data (452); and generating (408) an analysis (456) of the user's performance of the identified activity (454) based on the motion data (450) and the physiological data (452).

In the example of FIG. 7, however, identifying (406) an activity (454) of the user that corresponds to the motion data (450) and the physiological data (452) includes identifying (702) the activity (454) based on environmental condition data (750) and a historical activity pattern (752). Environmental condition data indicates a condition of an environment of the user that the user is experiencing. Environmental condition data may include any data indicating an environment that the user is experiencing. In a particular embodiment, environmental condition data may indicate weather conditions, such as humidity level, precipitation measurements, cloud coverage, and temperature. Environmental condition data may also indicate whether the user is inside or outside. For example, a user may provide input to the waistband monitoring device indicating that the user is indoors. In another embodiment, environmental condition data may be measured by the waistband monitoring device. For example, the waistband monitoring device may include a sensor that monitors humidity level or temperature surrounding the waistband monitoring device. In another embodiment, the waistband monitoring device may use one or more network interfaces to receive indications of environmental conditions, such as from a weather indication application, or from a local environmental condition indication device, such as a networked humidity and temperature sensor.

A historical activity pattern is an indication or log of the previous activities of the user. Non-limiting examples of the type of information contained within an historical activity pattern may include: the exercise activities the user performed in a particular time period, such as the last week; the times the activities were performed; duration of activities; environmental conditions; physiological state of user during activities; caloric intake of user; and recommended exercise activities provided to the user during a workout event. Identifying (702) the activity (454) based on environmental condition data (750) and a historical activity pattern (752) may be carried out by determining that the historical activity pattern indicates that user performed a particular activity when the environmental condition data indicated a particular condition; determining that the current environmental condition data indicates the particular condition; and in response to determining that the current environmental condition data indicates the particular condition, determining that the user is currently performing the particular activity identified in the historical activity pattern.

Figure 8:
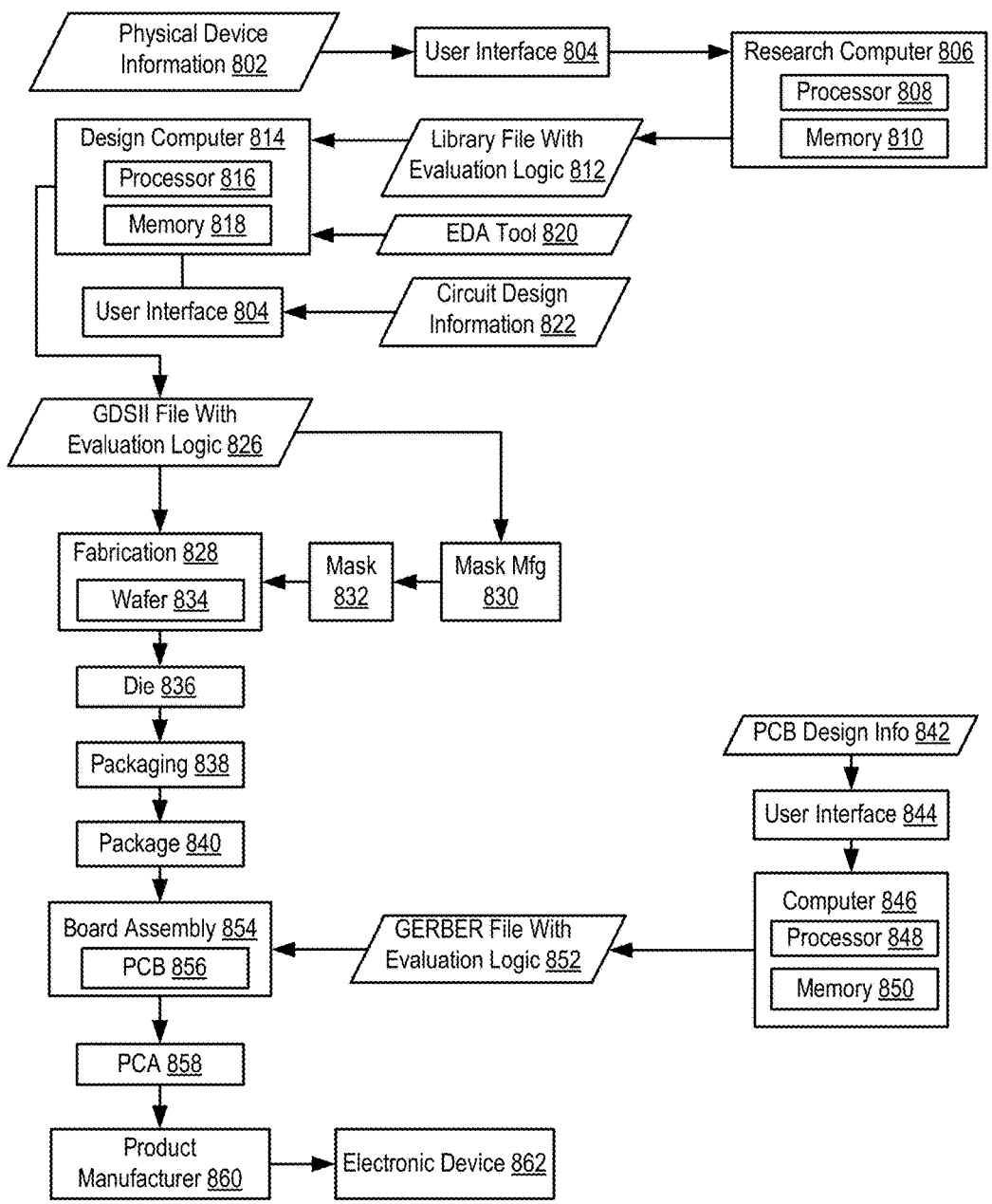
FIG. 8 sets forth a data flow diagram illustrating a manufacturing process for a device for waistband monitoring analysis for a user.

For further explanation, FIG. 8 sets forth a data flow diagram illustrating a manufacturing process (800) for a device that includes an analysis controller. Physical device information (802 is received at the manufacturing process (800), such as at a research computer (806). The physical device information (802) may include design information representing at least one physical property of a semiconductor device, such as a device that includes the analysis controller (199) of FIG. 1A (e.g., the waistband monitoring device (101) of FIG. 1A). For example, the physical device information (802) may include physical parameters, material characteristics, and structure information that is entered via a user interface (804) coupled to the research computer (806). The research computer (806) includes a processor (808), such as one or more processing cores, coupled to a computer readable medium such as a memory (810). The memory (810) may store computer readable instructions that are executable to cause the processor (808) to transform the physical device information (802) to comply with a file format and to generate a library file (812) containing evaluation logic for waistband monitoring analysis for a user.

In a particular embodiment, the library file (812) includes at least one data file including the transformed design information. For example, the library file (812) may include a library of semiconductor devices including a device that includes the analysis controller (199) of FIG. 1A (e.g., the waistband monitoring device (101) of FIG. 1A) that is provided to use with an electronic design automation (EDA) tool (820).

The library file (812) may be used in conjunction with the EDA tool (820) at a design computer (814) including a processor (816), such as one or more processing cores, coupled to a memory (818). The EDA tool (820) may be stored as processor executable instructions at the memory (818) to enable a user of the design computer (814) to design a circuit including a device that includes the analysis controller (199) of FIG. 1A (e.g., the waistband monitoring device (101) of FIG. 1A) of the library file (812). For example, a user of the design computer (814) may enter circuit design information (822) via a user interface (824) coupled to the design computer (814). The circuit design information (822) may include design information representing at least one physical property of a semiconductor device, such as a device that includes the analysis controller (199) of FIG. 1A (e.g., the waistband monitoring device (101) of FIG. 1A). To illustrate, the circuit design property may include identification of particular circuits and relationships to other elements in a circuit design, positioning information, feature size information, interconnection information, or other information representing a physical property of a semiconductor device.

The design computer (814) may be configured to transform the design information, including the circuit design information (822), to comply with a file format. To illustrate, the file formation may include a database binary file format representing planar geometric shapes, text labels, and other information about a circuit layout in a hierarchical format, such as a Graphic Data System (GDSII) file format. The design computer (814) may be configured to generate a data file including the transformed design information, such as a GDSII file (826) that includes information describing a device that includes evaluation logic used by the analysis controller (199) of FIG. 1A (e.g., the waistband monitoring device (101) of FIG. 1A) for waistband monitoring analysis for a user in addition to other circuits or information. To illustrate, the data file may include information corresponding to a system-on-chip (SOC) that includes a device that includes the analysis controller (199) of FIG. 1A (e.g., the waistband monitoring device (101) of FIG. 1A) and that also includes additional electronic circuits and components within the SOC.

The GDSII file (826) may be received at a fabrication process (828) to manufacture a device that includes the analysis controller (199) of FIG. 1A (e.g., the waistband monitoring device (101) of FIG. 1A) according to transformed information in the GDSII file (826). For example, a device manufacture process may include providing the GDSII file (826) to a mask manufacturer (830) to create one or more masks, such as masks to be used with photolithography processing, illustrated as a representative mask (832). The mask (832) may be used during the fabrication process to generate one or more wafers (834), which may be tested and separated into dies, such as a representative die (836). The die (836) includes a circuit including a device that includes the analysis controller (199) of FIG. 1A (e.g., the waistband monitoring device (101) of FIG. 1A).

The die (836) may be provided to a packaging process (838) where the die (836) is incorporated into a representative package (840). For example, the package (840) may include the single die (836) or multiple dies, such as a system-in-package (SiP) arrangement. The package (840) may be configured to conform to one or more standards or specifications, such as Joint Electron Device Engineering Council (JEDEC) standards.

Information regarding the package (840) may be distributed to various product designers, such as via a component library stored at a computer (846). The computer (846) may include a processor (848), such as one or more processing cores, coupled to a memory (850). A printed circuit board (PCB) tool may be stored as processor executable instructions at the memory (850) to process PCB design information (842) received from a user of the computer (846) via a user interface (844). The PCB design information (842) may include physical positioning information of a packaged semiconductor device on a circuit board, the packaged semiconductor device corresponding to the package (840) including a device that includes the analysis controller (199) of FIG. 1A (e.g., the waistband monitoring device (101) of FIG. 1A).

The computer (846) may be configured to transform the PCB design information (842) to generate a data file, such as a GERBER file (852) with data that includes physical positioning information of a packaged semiconductor device on a circuit board, as well as layout of electrical connections such as traces and vias, where the packaged semiconductor device corresponds to the package (840) including the analysis controller (199) of FIG. 1A. In other embodiments, the data file generated by the transformed PCB design information may have a format other than a GERBER format.

The GERBER file (852) may be received at a board assembly process (854) and used to create PCBs, such as a representative PCB (856), manufactured in accordance with the design information stored within the GERBER file (852). For example, the GERBER file (852) may be uploaded to one or more machines to perform various steps of a PCB production process. The PCB (856) may be populated with electronic components including the package (840) to form a representative printed circuit assembly (PCA) (858).

The PCA (858) may be received at a product manufacture process (860) and integrated into one or more electronic devices, such as a first representative electronic device (862) and a second representative electronic device (864). As an illustrative, non-limiting example, the first representative electronic device (862), the second representative electronic device (864), or both, may be selected from the group of a set top box, a music player, a video player, an entertainment unit, a navigation device, a communications device, a personal digital assistant (PDA), and a computer, into which the at least one controllable energy consuming module is integrated. As another illustrative, non-limiting example, one or more of the electronic devices (862) and (864) may be remote units such as wearable devices, mobile phones, hand-held personal communication systems (PCS) units, portable data units such as personal data assistants, global positioning system (GPS) enabled devices, navigation devices, or any other device that stores or retrieves data or computer instructions, or any combination thereof. Although FIG. 8 illustrates remote units according to teachings of the disclosure, the disclosure is not limited to these exemplary illustrated units. Embodiments of the disclosure may be suitably employed in any device which includes active integrated circuitry including memory and on-chip circuitry.

A device that includes the analysis controller (199) of FIG. 1A may be fabricated, processed, and incorporated into an electronic device, as described in the illustrative process (800). One or more aspects of the embodiments disclosed with respect to FIGS. 1-7 may be included at various processing stages, such as within the library file (812), the GDSII file (826), and the GERBER file (852), as well as stored at the memory (810) of the research computer (806), the memory (818) of the design computer (814), the memory (850) of the computer (846), the memory of one or more other computers or processors (not shown) used at the various stages, such as at the board assembly process (854), and also incorporated into one or more other physical embodiments such as the mask (832), the die (836), the package (840), the PCA (858), other products such as prototype circuits or devices (not shown), or any combination thereof. For example, the GDSII file (826) or the fabrication process (828) can include a computer readable tangible medium storing instructions executable by a computer, the instructions including instructions that are executed by the computer to perform the methods of FIGS. 4-7, or any combination thereof. Although various representative stages of production from a physical device design to a final product are depicted, in other embodiments fewer stages may be used or additional stages may be included. Similarly, the process (800) may be performed by a single entity, or by one or more entities performing various stages of the process (800).

Those of skill would further appreciate that the various illustrative logical blocks, configurations, modules, circuits, and method steps described in connection with the embodiments disclosed herein may be implemented as electronic hardware, computer software executed by a processing unit, or combinations of both. Various illustrative components, blocks, configurations, modules, circuits, and steps have been described above generally in terms of their functionality. Whether such functionality is implemented as hardware or executable processing instructions depends on the particular application and design constraints imposed on the overall system. Skilled artisans may implement the described functionality in varying ways with each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), a magnetoresistive random access memory (MRAM), a spin-torque-transfer MRAM (STT-MRAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method of waistband monitoring analysis, the method comprising:
   providing a waistband monitoring device coupled to a waistband worn around the waist of a user, the waistband monitoring device comprising one or more motion sensors and one or more physiological sensors in communication with an analysis controller, the waistband monitoring device integrated with the waistband;
   receiving, via the one or more motion sensors, motion data of the user;
   generating, by the analysis controller, a motion pattern based on the motion data received from the one or more motion sensors;
   receiving, by the analysis controller, physiological data generated by the one or more physiological sensors, wherein the physiological data indicates at least one vital sign of the user;
   identifying, by the analysis controller, one or more activities of the user that corresponds to the motion data and the physiological data, wherein an activity of the one or more of the activities is sleeping;
   comparing, by the analysis controller, the motion pattern to a predetermined activity pattern corresponding to the identified activity of the one or more activities of the user;
   evaluating, by the analysis controller, a user's performance of the identified activity by determining whether there are one or more differences between the motion pattern and the predetermined activity pattern;
   identifying, by the analysis controller, that there are one or more differences between the motion pattern and the predetermined activity pattern; and
   based on the determination, transmitting a visual output that displays an analysis of the user's performance of the identified activity based on the comparison between the motion pattern and the predetermined activity pattern, wherein the analysis comprises analyzing one or more of: a total time that the user was asleep, times that the user spent in sleep stages, a time for the user to fall asleep, and an indication of the amount that the user moved while asleep.

2. The method of claim 1 wherein comparing, by the analysis controller, the motion pattern to a predetermined activity pattern corresponding to the identified activity of the user, comprises:
   comparing the motion data used to generated the motion pattern with a stored motion pattern selected from a plurality of stored motion patterns, wherein each stored motion pattern is predefined to correspond with a particular activity.

3. The method of claim 1 wherein the one or more activities comprises a further activity that is a particular exercise activity and the analysis further comprises analyzing one or more of: a total time that the user spent performing the exercise activity and a caloric output that the user expended performing the exercise activity.

4. The method of claim 1 wherein identifying one or more activities of the user that corresponds to the motion data and the physiological data comprises:
   substantially matching to an activity pattern one of: the motion data and the physiological data.

5. The method of claim 1 wherein identifying one or more activities of the user that corresponds to the motion data and the physiological data comprises:
   identifying the activity based on environmental condition data and a historical activity pattern.

6. The method of claim 1 wherein the physiological data includes at least one of a hydration level measurement, a heart rate measurement, an ECG measurement, a respiration measurement, a pulse oximeter measurement, and a temperature of the user.

7. The method of claim 1 wherein the waistband monitoring device is within a pocket of the waistband.

8. The method of claim 1 wherein the waistband monitoring device is coupled to the waistband via an attachment.

9. A waistband monitoring device for coupling to a waistband of a user to perform waistband monitoring analysis of the user, the waistband monitoring device comprising one or more motion sensors and one or more physiological sensors in communication with an analysis controller, the analysis controller comprising a computer processor and computer memory operatively coupled to the computer processor, the computer memory having disposed within it computer program instructions that, when executed by the computer processor, cause the apparatus to perform an operation, comprising:
   receiving, via the one or more motion sensors, motion data of the user;
   generating a motion pattern based on the motion data received from the one or more motion sensors;
   receiving physiological data generated by the one or more physiological sensors, wherein the physiological data indicates at least one vital sign of the user;
   identifying one or more activities of the user that corresponds to the motion data and the physiological data, wherein an activity of the one or more activities is sleeping;
   comparing the motion pattern to a predetermined activity pattern corresponding to the identified activity of the one or more activities of the user;
   evaluating a user's performance of the identified activity by determining whether there are one or more differences between the motion pattern and the predetermined activity pattern;
   identifying that there are one or more differences between the motion pattern and the predetermined activity pattern; and
   based on the determination, transmitting a visual output that displays an analysis of the user's performance of the identified activity based on the comparison between the motion pattern and the predetermined activity pattern, wherein the analysis comprises analyzing one or more of: a total time that the user was asleep, times that the user spent in sleep stages, a time for the user to fall asleep, and an indication of the amount that the user moved while asleep.

10. The apparatus of claim 9 wherein comparing the motion pattern to the predetermined activity pattern corresponding to the identified activity of the user, comprises:
   comparing the motion data with a stored motion pattern selected from a plurality of stored motion patterns, wherein each stored motion pattern is predefined to correspond with a particular activity.

11. The apparatus of claim 9 wherein the one or more activities comprises a further activity that is a particular exercise activity and the analysis further comprises analyzing one or more of: a total time that the user spent performing the exercise activity and a caloric output that the user expended performing the exercise activity.

12. The apparatus of claim 9 wherein identifying one or more activities of the user that corresponds to the motion data and the physiological data comprises:
   substantially matching to an activity pattern one of: the motion data and the physiological data.

13. The apparatus of claim 9 wherein identifying one or more activities of the user that corresponds to the motion data and the physiological data comprises:
   identifying the activity based on environmental condition data and a historical activity pattern.

14. The apparatus of claim 9 wherein the physiological data includes at least one of a hydration level measurement, a heart rate measurement, an ECG measurement, a pulse oximeter measurement, a respiration measurement, and a temperature of the user.

15. A non-transitory computer readable storage medium in communication with one or more motion sensors and one or more physiological sensors, the non-transitory computer readable medium including one or more sequences of instructions, which, when executed by one or more processors, cause the one or more processors to perform operations, comprising:
   receiving, via the one or more motion sensors, motion data of the user;
   generating a motion pattern based on the motion data received from the one or more motion sensors;
   receiving physiological data generated by the one or more physiological sensors, wherein the physiological data indicates at least one vital sign of the user;
   identifying one or more activities of the user that corresponds to the motion data and the physiological data, wherein an activity of the one or more activities is sleeping;
   comparing the motion pattern to a predetermined activity pattern corresponding to the identified activity of the one or more activities of the user;
   evaluating a user's performance of the identified activity by determining whether there are one or more differences between the motion pattern and the predetermined activity pattern;
   identifying that there are one or more differences between the motion pattern and the predetermined activity pattern; and
   based on the determination, transmitting a visual output that displays an analysis of the user's performance of the identified activity based on the comparison between the motion pattern and the predetermined activity pattern, wherein the analysis comprises analyzing one or more of: a total time that the user was asleep, times that the user spent in sleep stages, a time for the user to fall asleep, and an indication of the amount that the user moved while asleep.

16. The non-transitory computer readable storage medium of claim 15 wherein comparing the motion pattern to a predetermined activity pattern corresponding to the identified activity of the user, comprises:
   comparing the motion data used to generated the motion pattern with a stored motion pattern selected from a plurality of stored motion patterns, wherein each stored motion pattern is predefined to correspond with a particular activity.

17. The non-transitory computer readable storage medium of claim 15 wherein the one or more activities comprises a further activity that is a particular exercise activity and the one or more indications of the analysis further comprises analyzing one or more of: a total time that the user spent performing the exercise activity and a caloric output that the user expended performing the exercise activity.

* * * * *